US007078579B2

(12) United States Patent
Doll et al.

(10) Patent No.: US 7,078,579 B2
(45) Date of Patent: *Jul. 18, 2006

(54) PROCESS FOR THE ISOMERIZATION OF A VINYLIDENE OLEFIN

(75) Inventors: Michael Joseph Doll, Katy, TX (US); Brendan Dermot Murray, Houston, TX (US)

(73) Assignee: Shell Oil Company, Houston, TX (US)

( * ) Notice: Subject to any disclaimer, the term of this patent is extended or adjusted under 35 U.S.C. 154(b) by 655 days.

This patent is subject to a terminal disclaimer.

(21) Appl. No.: 10/166,402

(22) Filed: Jun. 10, 2002

(65) Prior Publication Data

US 2003/0009071 A1    Jan. 9, 2003

Related U.S. Application Data

(60) Provisional application No. 60/300,043, filed on Jun. 21, 2001.

(51) Int. Cl.
*C07C 5/23* (2006.01)
(52) U.S. Cl. ..................... 585/666; 585/664
(58) Field of Classification Search ............... 585/664, 585/666, 377
See application file for complete search history.

(56) References Cited

U.S. PATENT DOCUMENTS

| | | | | |
|---|---|---|---|---|
| 2,217,252 | A | 10/1940 | Hoog | 260/683 |
| 3,150,202 | A | 9/1964 | Holt et al. | 260/683.2 |
| 3,173,968 | A | 3/1965 | Edwards et al. | 260/683.2 |
| 3,686,250 | A | 8/1972 | Lanier | 260/448 A |
| 3,720,628 | A | 3/1973 | Hayes et al. | 252/442 |
| 4,020,121 | A | 4/1977 | Kister et al. | 260/683.15 D |
| 4,024,189 | A | 5/1977 | Davis | 260/585 A |
| 4,214,087 | A | 7/1980 | Fanelli et al. | 546/319 |
| 4,247,719 | A | 1/1981 | Buck et al. | 568/750 |
| 4,260,844 | A | 4/1981 | O'Donnell et al. | 585/523 |
| 4,284,837 | A | 8/1981 | Lutz | 585/523 |
| 4,293,728 | A | 10/1981 | Montgomery | 585/670 |
| 4,472,522 | A | 9/1984 | Singleton | 502/108 |
| 4,472,525 | A | 9/1984 | Singleton | 502/155 |
| 4,528,416 | A | 7/1985 | Lutz | 585/527 |
| 4,697,040 | A | 9/1987 | Williamson et al. | 585/666 |
| 4,727,203 | A | 2/1988 | Hamilton, Jr. | 585/329 |
| 4,749,819 | A | 6/1988 | Hamilton, Jr. | 585/329 |
| 4,814,531 | A | 3/1989 | Cullo et al. | 585/467 |
| 4,822,911 | A | 4/1989 | Fried | 560/205 |
| 4,836,911 | A | 6/1989 | Skeels et al. | 208/111 |
| 4,849,576 | A | 7/1989 | Nowack et al. | 585/670 |
| 4,906,793 | A | 3/1990 | Cullo et al. | 568/804 |
| 4,996,385 | A | 2/1991 | Cullo et al. | 585/640 |
| 5,087,793 | A | 2/1992 | Akiyama et al. | 585/666 |
| 5,095,172 | A | 3/1992 | Lanier et al. | 585/851 |
| 5,107,047 | A | 4/1992 | Del Rossi et al. | 585/666 |
| 5,237,120 | A | 8/1993 | Haag et al. | 585/666 |
| 5,304,601 | A * | 4/1994 | Des Courieres et al. | 502/66 |
| 5,557,027 | A | 9/1996 | Kemp | 585/527 |
| 5,789,646 | A | 8/1998 | Romera et al. | 585/833 |
| 5,817,907 | A | 10/1998 | Benazzi et al. | 585/671 |
| 6,407,302 | B1 * | 6/2002 | Twu et al. | 585/670 |

FOREIGN PATENT DOCUMENTS

| | | |
|---|---|---|
| DE | 293967 A5 | 6/1989 |
| EP | 0009894 | 1/1982 |
| EP | 0037671 B1 | 3/1983 |
| GB | 934783 | 8/1963 |
| NL | 8800685 | 10/1989 |
| ZA | 92/03798 | 5/1992 |

OTHER PUBLICATIONS

W. M. Meier and D. H. Olson, "Atlas of Zeolite Structure Types," 2nd revised edition (1987), published by the Structure Commission of the International Zeolite Association, pp. 18-19, 62-63, 100-101.
H. van Bekkum, E. M. Flanigen, J.C. Jansen (Ed.), "Introduction into Zeolite Science and Practice" Elsevier Science Publishers (1991), p. 642.
"Ullmann's Encyclopedia of Industrial Chemistry," 5th revised edition, vol. A28, pp. 475-504.
U.S. Appl. No. 10/165,909, filed Jun. 10, 2002, Doll et al.
Kirk Othmer, Encyclopedia of Chemical Technology, 4th edition, vol. 16, pp. 888-925.
Kirk Othmer, Encyclopedia of Chemical Technology, 3rd edition, vol. 15, pp. 639, 660.
Kirk Othmer, Encyclopedia of Chemical Technology, 3rd edition, vol. 7, pp. 849-851.
K. Dorfner (Ed.) "Ion Exchangers," (1991), p. 987.
Product Information No. 128 of Rohm and Haas Co., "Ion Exchange Catalysis and Matrix Effects," May 1988.
International Search Report of PCT/EP 02/06894 of Oct. 31, 2002.

(Continued)

*Primary Examiner*—Glenn Caldarola
*Assistant Examiner*—In Suk Bullock

(57) ABSTRACT

A process for the double bond isomerization of a vinylidene olefin, comprising contacting a feed comprising the vinylidene olefin with an isomerization catalyst which comprises a molecular sieve in an acidic form, which molecular sieve comprises pores which have a pore size of more than 0.6 nm; and a process for treating an olefin mixture which comprises a linear α-olefin and a vinylidene olefin which is isomeric to the linear α-olefin and which is of the general formula $CH_2=C(R^1)R^2$, wherein $R^1$ represents an ethyl group and $R^2$ represents a linear 1-alkyl group, which process comprises isomerizing the vinylidene olefin to form a double bond isomer of the vinylidene olefin by contacting a feed comprising the olefin mixture with an isomerization catalyst which comprises a molecular sieve in an acidic form, which molecular sieve comprises pores which have a pore size of more than 0.6 nm, and separating the linear α-olefin from the double bond isomer of the vinylidene olefin.

17 Claims, No Drawings

OTHER PUBLICATIONS

International Preliminary Examination Report of PCT/EP02/06893 of Sep. 18, 2003.

International Preliminary Examination Report of PCT/EP02/06894 of Sep. 23, 2003.

* cited by examiner

PROCESS FOR THE ISOMERIZATION OF A VINYLIDENE OLEFIN

This application claims the benefit of U.S. Provisional Application No. 60/300,043 filed Jun. 21, 2001, the entire disclosure of which is hereby incorporated by reference.

FIELD OF THE INVENTION

The invention relates to a process of the double bond isomerization of a vinylidene olefin, comprising contacting a feed comprising the vinylidene olefin with an isomerization catalyst which comprises a molecular sieve.

As used herein, the term "double bond isomerization" relates to a shift of a double bond in the molecular structure of an olefin from a thermodynamically less favorable position to a thermodynamically more favorable position. An example of a double isomerization is a shift of the double bond of a linear α-olefin from the external, α-position to an internal position, for example a β- or γ-position. Another example is a shift of one or two double bonds of a non-conjugated diolefin to form a conjugated diolefin. Again another example is a shift of the double bond of a vinylidene olefin to form a tri-substituted ethene, e.g. the isomerization of 2-ethyl-1-hexene to 3-methyl-2-heptene or 3-methyl-3-heptene.

BACKGROUND OF THE INVENTION

U.S. Pat. No. 5,789,646 discloses a process for the double bond isomerization of a vinylidene olefin, comprising contacting a feed comprising the vinylidene olefin with an isomerization catalyst which comprises a molecular sieve which is a zeolite in the hydrogen form. The zeolite specifically disclosed is an H-ZSM-5 having a silicon/aluminum atomic ratio of 25. The pore size of H-ZSM-5 is that of the two channels which interconnect, viz. channels of 0.53× 0.56 nm diameter and channels of 0.51×0.51 nm diameter (cf. W M Meier and D H Olson, "Atlas of Zeolite Structure Types", $2^{nd}$ Revised edition (1987), published by the Structure Commission of the International Zeolite Association, p. 100–101). U.S. Pat. No. 5,789,646 considers the influence of the acidity of a solid acid on its performance as a catalyst in the vinylidene isomerization and suggests that accordingly the catalysts may be positioned on an acidity scale. It is striking that in the working examples of U.S. Pat. No. 5,789,646 the results reported for the H-ZSM-5 catalyst and for a crosslinked sulfonic acid catalyst are "essentially identical", which would suggest that widely different solid acid catalysts are essentially equally positioned on the acidity scale.

U.S. Pat. No. 4,697,040 discloses a process for the double bond isomerization of a vinylidene olefin, comprising contacting a feed comprising the vinylidene olefin with an isomerization catalyst which comprises a molecular sieve which is a zeolite in the sodium form. The zeolite of U.S. Pat. No. 4,697,040 is a specific Y type zeolite, designated LZ-Y52 (trademark), which has a pore or channel size of 0.74 nm (cf. W M Meier and D H Olson, "Atlas of Zeolite Structure Types", $2^{nd}$ Revised edition (1987), published by the Structure Commission of the International Zeolite Association, p. 62–63).

SUMMARY OF THE INVENTION

The present invention provides molecular sieve catalysts for the double bond isomerization of vinylidene olefins which have an improved performance compared with the prior art molecular sieve catalysts. The improved catalyst performance may be seen in one or more aspects, such as an improved catalyst activity, an improved selectivity, an improved catalyst stability with respect to activity and an improved catalyst stability with respect to selectivity. In this context, selectivity may be seen in various ways, for example in the formation of the double bond isomer of the vinylidene olefin in question relative to the formation of other compounds from the vinylidene olefin, for example dimers, trimers, skeletal isomers, etc., or in the formation of one or more isomers from the vinylidene olefin in question relative to the conversion of other compounds present in the feed.

The isomerization catalysts provided by the present invention comprise a molecular sieve in an acidic form which has a large pore size, for example of at least 0.6 nm. This is unexpected because such large pore size acidic molecular sieves would be expected to promote the conversion of olefins into undesired isomers and/or dimers and trimers, which tend to diffuse only slowly within the molecular sieve channels giving rise not only to a lower selectivity but also to more degradation, more carbonization and therefore a more rapid deterioration of the catalyst performance, i.e. less catalyst stability.

Accordingly, the present invention provides a process for the double bond isomerization of a vinylidene olefin, comprising contacting a feed comprising the vinylidene olefin with an isomerization catalyst which comprises a molecular sieve in an acidic form, which molecular sieve comprises pores which have a pore size of more than 0.6 nm.

The process of this invention may very usefully be applied to effect the isomerization of a specific type of vinylidene olefin in admixture with a linear α-olefin which is isomeric to the vinylidene olefin. In the isomerization the linear α-olefin is not or virtually not converted. The specific vinylidene olefin in question is of the general formula $CH_2$=$C(R^1)R^2$, wherein $R^1$ represents an ethyl group and $R^2$ represents a linear 1-alkyl group. Such combination of olefins may be present in the reaction product of an ethene oligomerization process, wherein the linear α-olefin is the main product and the vinylidene olefin is a byproduct. The boiling points of the linear α-olefin and the vinylidene olefin are generally so close that their separation by distillation represents a problem. The isomerization of the vinylidene olefin then leads to a vinylidene olefin isomer which can more readily be separated from the linear α-olefin than the vinylidene olefin itself (cf. U.S. Pat. No. 5,789,646 and U.S. Pat. No. 4,697,040, of which the teachings are incorporated herein by reference).

Accordingly, the present invention also provides a process for treating an olefin mixture which comprises a linear α-olefin and a vinylidene olefin which is isomeric to the linear α-olefin and which is of the general formula $CH_2$=$C(R^1)R^2$, wherein $R^1$ represents an ethyl group and $R^2$ represents a linear 1-alkyl group, which process comprises isomerizing the vinylidene olefin to form a double bond isomer of the vinylidene olefin by contacting a feed comprising the olefin mixture with an isomerization catalyst which comprises a molecular sieve in an acidic form, which molecular sieve comprises pores which have a pore size of more than 0.6 nm, and separating the linear α-olefin from the double bond isomer of the vinylidene olefin.

DETAILED DESCRIPTION OF THE INVENTION

The process of this invention is suitable for effecting the isomerization of a wide range of vinylidene olefins. The vinylidene olefins may be of the general formula $CH_2=C(R^1)R^2$, wherein $R^1$ and $R^2$ represent alkyl groups independently having at least 2 carbon atoms, such that the molecular structure comprises at least one allylic hydrogen atom. Typically, $R^1$ and $R^2$ represent alkyl groups independently having at most 20 carbon atoms, more typically at most 16 carbon atoms. Typically, $R^1$ represents an ethyl group. Typically, $R^2$ represents a linear 1-alkyl group, which preferably comprises an even number of carbon atoms. Preferred vinylidene olefins are for example 2-ethyl-1-pentene and 2-ethyl-1-heptene, in particular 2-ethyl-1-butene, 2-ethyl-1-hexene, 2-ethyl-1-octene, 2-ethyl-1-decene and 2-ethyl-1-dodecene.

The vinylidene olefin may be a plurality of vinylidene olefins, in particular a plurality of vinylidene olefins which each carry in their molecular structure alkyl groups $R^1$ representing ethyl groups and which differ from each other in the alkyl groups $R^2$. Preferably, the alkyl groups $R^2$ are linear 1-alkyl groups having carbon numbers which differ from each other by two (for example 5, 7 and 9) and preferably these carbon numbers are even numbers (for example 4 and 6; or 4, 6, 8 and 10; or 12, 14 and 16).

A second olefin may be present in the isomerization, which is relatively stable and does not isomerise or react otherwise under the prevailing conditions, or only to a low extent. Examples of the second olefin are ethene, propene, cyclohexene and 2-methylpropene.

It is a particular aspect of the present invention that the vinylidene olefin can be isomerised in the presence of a linear α-olefin, as the second olefin, whereby the linear α-olefin is not or virtually not isomerised or otherwise reacted. Preferably, the linear α-olefin has the same carbon number as the vinylidene olefin, so that the linear α-olefin represents an isomer of the vinylidene olefin. In particular, the vinylidene olefin carries in its molecular structure an alkyl group $R^1$ representing an ethyl group and the alkyl group $R^2$ is a linear 1-alkyl group. For example, 2-ethyl-1-butene may be isomerised in the presence of 1-hexene, 2-ethyl-1-hexene may be isomerised in the presence of 1-octene and 2-ethyl-1-octene may be isomerised in the presence of 1-decene. Two or more such vinylidene olefins may be isomerised in the presence of the corresponding, isomeric linear α-olefins.

The isomerization catalyst comprises a molecular sieve in an acidic form, which molecular sieve comprises pores which have a pore size of more than 0.6 nm.

Preferably, the pore size of the molecular sieve of the isomerization catalyst is at least 0.65 nm, more preferably at least 0.7 nm. Typically the pore size of the molecular sieve of the isomerization catalyst is at most 1 nm, more typically at most 0.9 nm, preferably at most 0.8 nm. When the pores or channels of the molecular sieve are not circular, the pore size is herein deemed to relate to the smaller width of the pores or channels. The pore size of many of such molecular sieves has been specified in W M Meier and D H Olson, "Atlas of Zeolite Structure Types", 2$^{nd}$ Revised edition (1987), published by the Structure Commission of the International Zeolite Association. The terms "pore" and "channel" as used herein in relation to molecular sieves are exchangeable.

The molecular sieve of the isomerization catalyst may typically be a silica-aluminophosphate molecular sieve or a metal silica-aluminophosphate molecular sieve, in which the metal may be for example iron, cobalt or nickel.

Preferably, the molecular sieve of the isomerization catalyst is an aluminosilicate, i.e. a zeolite, typically having a silicon/aluminum (Si/Al) atomic ratio of at least 1.3, more preferably at least 1.5, in particular at least 2. Preferably, the Si/Al atomic ratio is at most 20, more preferably at most 8, in particular at most 5. As used herein, unless mentioned otherwise, the Si/Al atomic ratio is the skeletal Si/Al atomic ratio of the zeolite. The skeletal Si/Al atomic ratio is deemed to be determined by $^{29}$Si-NMR.

Typically, the molecular sieve of the isomerization catalyst comprises sodalite cages in its molecular structure. Preferably, the sodalite cages are arranged in a faujasite structure. Mordenite zeolites, beta-zeolites and omega-zeolites may be used, however, when the vinylidene olefin is of the general formula as defined hereinbefore wherein $R^1$ represents an ethyl group and $R^2$ represents a linear 1-alkyl group, in particular having an even number of carbon atoms, it is preferred that the isomerization catalyst comprises a molecular sieve other than a mordenite zeolite in the ammonium form.

The molecular sieve of the isomerization catalyst is in an acidic form, for example in the ammonium form or in the hydrogen form. This means that the cationic sites of the molecular sieve of the isomerization catalyst are at least partly occupied by acidic species, for example ammonium and/or hydrogen ions. Preferably, the cationic sites of the molecular sieve of the isomerization catalyst are at least partly occupied by hydrogen ions, i.e. the molecular sieve is in the hydrogen form. Other cationic cites may be occupied by, for example alkali metal ions or alkaline earth metal ions, such as sodium ions or calcium or magnesium ions. Suitably at least 10%, more suitably at least 50%, in particular at least 75% of the cationic sites is occupied by hydrogen and/or ammonium ions, whilst in practice frequently at most 99.9%, more frequently at most 99% of the cationic sites is occupied by hydrogen and/or ammonium ions. Preferably at least 10%, more preferably at least 50%, in particular at least 75% of the cationic sites is occupied by hydrogen ions, whilst in practice frequently at most 99.9%, more frequently at most 99% of the cationic sites is occupied by hydrogen ions.

If the molecular sieve for use in the isomerization catalyst is in the ammonium form, it may be converted into the hydrogen form prior to its use by any suitable means, for example by heating at a temperature of at least 300° C., for example at a temperature in the range of from 400 to 600° C.

Typically the molecular sieve of the isomerization catalyst has a surface area in the range of from 400 to 1000 m$^2$/g, more typically from 600 to 950 m$^2$/g. As used herein, the surface area is deemed to have been measured by the method of ASTM-D3663-92.

An example of a suitable molecular sieve for use in the isomerization catalyst is CBV 500 (trademark), which is a zeolite having a faujasite structure, a bulk Si/Al atomic ratio of about 2.6 (the skeletal Si/Al atomic ratio is believed to be in the range of 2.3–3), a pore size of 0.74 nm and a surface area of about 750 m$^2$/g. CBV 500 zeolite is available in the ammonium form, marketed by Zeolyst International. Another example of a suitable molecular sieve for use in the isomerization catalyst is CBV 400 (trademark), which is a zeolite having a faujasite structure, a bulk Si/Al atomic ratio of about 2.55 (the skeletal Si/Al atomic ratio is believed to be in the range of 2.3–3), a pore size of 0.74 nm and a surface area of about 730 m$^2$/g. CBV 400 zeolite is available in the hydrogen/sodium form (containing 2.2% w of sodium, calculated as Na$_2$O, which is believed to pertain to 80–85% of the cationic sites being occupied by hydrogen ions). CBV 400 zeolite is marketed by Zeolyst International.

It is preferred that the molecular sieve for use in the isomerization catalyst is in the form of particles, for example pellets, cylinders or beads, which comprise for example at least 10% w, typically at least 50% w, preferably at least 90% w of the molecular sieve, based on the weight of the particles. In practice such particles comprise frequently at most 99.99% w, more frequently at most 99.9% w, most frequently at most 99% w of the molecular sieve, based on the weight of the particles. A conventional binder may be present in the particles. Useful conventional binders may be inorganic materials, such as clay, silica and/or metal oxides. The molecular sieve for use in the isomerization catalyst may be compounded with other materials, such as porous matrix materials, for example, alumina, silica/alumina, silica/magnesia, silica/zirconia and silica/titania, silica/alumina/thoria and silica/alumina/zirconia.

In the present isomerization process a liquid diluent may or may not be present. Suitable are organic liquid diluents, for example hydrocarbons, such as alkanes, cycloalkanes and aromatics, or chlorohydrocarbons.

The present isomerization process may be conducted by contacting the feed as a liquid phase with the isomerization catalyst. The feed comprises as components the vinylidene olefin to be isomerised and optionally the second olefin (for example the linear α-olefin) and optionally the liquid diluent. Suitably, the vinylidene olefin represents from 0.01% w to 100% w of the feed. More suitably the vinylidene olefin represents from 0.05 % w to 90% w of the feed. The second olefin, if present, represents suitably from 10% w to 99.99% w of the feed, more suitably from 20% w to 99.95% w of the feed. The weight ratio of the vinylidene olefin to the second olefin, if present, is preferably in the range of from 0.05:100 to 10:100, in particular from 0.1:100 to 5:100. The liquid diluent, if present, represents suitably from 1% w to 99.99% w of the mixture of components, more suitably from 10% w to 99.95% w of the feed. Substances being present in smaller quantities are normally not considered to be diluents.

The present isomerization process may be carried out with the isomerization catalyst suspended in the feed, which is especially suitable when the isomerization process is carried out as a batch liquid phase process. The quantity of isomerization catalyst suspended may be in the range of from 0.1 to 20 g/kg feed, preferably from 0.5 to 10 g/kg feed.

As an alternative, the isomerization process may be carried out with the isomerization catalyst present as a fixed bed, which is especially suitable when the isomerization process is carried out as a continuous process, whether as a liquid phase process or as a gas phase process. A continuous liquid phase process employing a fixed bed is preferred. The LHSV may be in the range of from 0.01 to 200 kg/(l.h), preferably from 0.1 to 100 kg/(l.h). In this context, the term "LHSV" stands for the liquid hourly space velocity which is the mass flow rate divided by the volume of the catalyst bed. The direction of flow through the catalyst bed is not material. For example, the direction of flow may be up-flow or down-flow.

The present isomerization process may be carried out within wide ranges of pressures and temperatures which can effect the desired isomerization. The pressure is suitably in the range of from 0.01 to 10 MPa, more suitably in the range of from 0.02 to 2 MPa, in particular from 0.05 to 1 MPa. Suitably the temperature is in the range of from 0 to 150° C., more suitably in the range of from 10 to 100° C., most suitably in the range of from 20 to 80° C.

The isomerization process may be carried out such that the conversion of the vinylidene olefin over the isomerization catalyst is at least 5%. It is preferred that the conversion of the vinylidene olefin is at least 40%, more preferably at least 60%, most preferably at least 80%. Frequently the conversion of the vinylidene olefin is complete, however, more frequently the conversion of the vinylidene olefin at most 99.9%, most frequently at most 99.8%. When an α-olefin is present, in particular a linear α-olefin, the conversion of the α-olefin over the isomerization catalyst is preferably at most 20%, more preferably at most 10%, most preferably at most 5%. Frequently, the α-olefin is not converted at all, more frequently the conversion of the α-olefin is at least 0.1%, more frequently at least 0.2%.

It is preferred that one or more of the vinylidene olefin, the second olefin, if present, and the liquid diluent, if present, are pretreated before being contacted with the isomerization catalyst. Suitable methods of pretreating are distillation, extraction and, in particular, contacting with a pretreating material. Combinations of such methods may be applied. Suitable pretreating materials are for example active carbon, alumina, silica and zeolites. The pretreatment may be applied to one or more separate, individual components of the feed. However, it is preferred to pretreat them together as a mixture, in particular as the feed to the isomerization process, prior to contacting with the isomerization catalyst.

Without wishing to be bound by theory, it is believed that the pretreatment leads to the removal of impurities which could be detrimental to the performance of the isomerization catalyst, in particular the catalyst's activity and activity stability. Conceivably, such impurities may be water or organic compounds comprising heteroatoms, such as oxygen, nitrogen, sulfur and phosphorus. Such impurities may have been introduced during the synthesis, work-up, purification or other processing of the individual components.

Typically, upon contacting with the isomerization catalyst, the feed comprises water at a level of at most 50 ppmw, preferably at most 10 ppmw, in particular at most 1 ppmw, relative to the weight of the feed. Typically, the content of organic compounds comprising oxygen heteroatoms is such that the content of the oxygen heteroatoms is at most 50 ppmw, preferably at most 20 ppmw, relative to the weight of the feed. Typically, the content of organic compounds comprising nitrogen heteroatoms is such that the content of the nitrogen heteroatoms is at most 50 ppmw, preferably at most 20 ppmw, relative to the weight of the feed. Typically, the content of organic compounds comprising sulfur heteroatoms is such that the content of the sulfur heteroatoms is at most 50 ppmw, preferably at most 20 ppmw, relative to the weight of the feed. Typically, the content of organic compounds comprising phosphorus heteroatoms is such that the content of the phosphorus heteroatoms is at most 10 ppmw, preferably at most 2 ppmw, relative to the weight of the feed. Such levels of contents of impurities may be achieved by applying the pretreatment.

A preferred zeolite for use as the pretreating material is a zeolite having a pore size of at least 0.3 nm, or at least 0.35 nm, in particular at least 0.5 nm, and most in particular at least 0.6 nm, and typically it has a pore size of at most 1.5 nm, more typically at most 1.2 nm, in particular at most 1 nm. The pore size of many of such zeolites has been specified in W M Meier and D H Olson, "Atlas of Zeolite Structure Types", 2$^{nd}$ Revised edition (1987), published by the Structure Commission of the International Zeolite Association.

Preferably, the zeolite for use as the pretreating material comprises sodalite cages in its structure, in particular sodalite cages which are arranged such as to form a faujasite structure. Preferably, the zeolite for use as the pretreating material has a Si/Al atomic ratio of above 1, in particular at least 1.2. Preferably, the Si/Al atomic ratio of at most 1.5. Preferably, the zeolite for use as the pretreating material is a zeolite-X.

The zeolite for use as the pretreating material typically comprises ions of an alkali metal and/or ions of an alkaline earth metal occupying at least a part of the cationic sites. Alkali metal ions are preferred, in particular sodium ions. Examples of suitable alkaline earth metal ions are calcium ions and magnesium ions. Suitably at least 10%, more suitably at least 50%, in particular at least 90% of the cationic sites is occupied by ions of an alkali metal and/or ions of an alkaline earth metal, whilst in practice frequently at most 99.9%, more frequently at most 99% of the cationic sites is occupied by ions of an alkali metal and/or ions of an alkaline earth metal. Preferably at least 10%, more preferably at least 50%, in particular at least 90% of the cationic sites is occupied by alkali metal ions, whilst in practice frequently at most 99.9%, more frequently at most 99% of the cationic sites is occupied by alkali metal ions.

Typically the zeolite for use as the pretreating material has a surface area in the range of from 400 to 1000 $m^2/g$, more typically from 600 to 950 $m^2/g$.

Examples of preferred zeolites for use as the pretreating material are zeolite-10X, in particular zeolite-13X. These zeolites are readily commercially available, for example from UOP. Zeolite-10X is an X type zeolite in the calcium form which has a pore size of about 0.75 nm, a Si/Al atomic ratio in the range of from 1.2 to 1.5 and a surface area of about 700 $m^2/g$. Zeolite-13X is an X type zeolite in the sodium form which has a pore size of about 8 nm, a Si/Al atomic ratio in the range of from 1.2 to 1.5 and a surface area of about 700 $m^2/g$.

It is preferred that the zeolite for use as the pretreating material is in the form of particles, for example pellets, cylinders or beads, which comprise for example at least 10% w, typically at least 50% w, preferably at least 90% w of the zeolite, based on the weight of the particles. In practice such particles comprise frequently at most 99.99% w, more frequently at most 99.9% w, most frequently at most 99% w of the zeolite, based on the weight of the particles. A conventional binder may be present in the particles. Useful conventional binders may be inorganic materials, such as clay, silica and/or metal oxides. The zeolite for use as the pretreating material may be compounded with other materials, such as porous matrix materials, for example, alumina, silica/alumina, silica/magnesia, silica/zirconia and silica/titania, silica/alumina/thoria and silica/alumina/zirconia.

The pretreatment may be carried out by suspending the pretreating material in the component in question or the mixture of components, which is especially suitable when the pretreatment is carried out as a batch liquid phase process. The quantity of the pretreating material suspended may be in the range of from 0.1 to 50 g/kg component or mixture of components, preferably from 0.2 to 10 g/kg component or mixture of components.

As an alternative, the pretreatment may be carried out with the pretreating material present as a fixed bed, which is especially suitable when the pretreatment process is carried out as a continuous process, whether as a liquid phase process or as a gas phase process. A continuous liquid phase process employing a fixed bed is preferred. The LHSV may be in the range of from 0.05 to 50 kg/(l.h), preferably from 0.1 to 20 kg/(l.h). In this context, the term "LHSV" stands for liquid hourly space velocity which is the mass flow rate divided by the volume of the pretreating bed. The direction of flow through the pretreating bed is not material. For example, the direction of flow may be up-flow or down-flow.

The pretreatment using the pretreating material may be carried out within wide ranges of temperatures and pressures. Suitably the temperature is in the range of from −20 to 100° C., more suitably in the range of from −10 to 80° C. The pressure is suitably in the range of from 0.01 to 10 MPa, more suitably in the range of from 0.02 to 2 MPa, in particular in the range of from 0.05 to 1 MPa.

As set out hereinbefore, in certain embodiments the isomerization process of this invention is applied to one or more vinylidene olefins in admixture with the respective isomeric linear α-olefin(s). In the molecular structure of the vinylidene olefins in question the alkyl groups $R^1$ are ethyl groups and the alkyl groups $R^2$ are linear 1-alkyl groups having an even carbon number, or having consecutive even carbon numbers. Such mixtures may be obtained from ethene oligomerization processes, wherein the one or more linear α-olefins is the main product and the one or more vinylidene olefins are by products. Such ethene oligomerization processes are known in the art, for example, from U.S. Pat. No. 4,749,819, U.S. Pat. No. 5,557,027, U.S. Pat. No. 4,528,416, U.S. Pat. No. 4,472,525, U.S. Pat. No. 4,472,522, U.S. Pat. No. 4,284,837, U.S. Pat. No. 4,260,844 and U.S. Pat. No. 4,020,121, of which the teachings are incorporated herein by reference.

The ethene oligomerization process may be carried out in the presence of Ziegler type catalyst such as lithium, sodium, potassium, beryllium and magnesium metal catalysts. Suitably, the ethene oligomerization process is carried out in the presence of a nickel catalyst, wherein the nickel is complexed with a bidentate chelating ligand. Preferred bidentate chelating ligands have a tertiary organophosphorus moiety with a suitable functional group substituted on a carbon atom attached directly to or separated by no more than two carbon atoms from the phosphorus atom of the organophosphorus moiety. Examples of preferred bidentate chelating ligands are o-dihydrocarbylphosphinobenzoic acids, e.g. o-diphenyl-phosphinobenzoic acid and o-dicyclohexylphosphinobenzoic acid, and 2-dihydrocarbylphosphinopropionic acids, e.g. 2-diphenylphosphinopropionic acid and 2-dicyclohexyl-phosphinopropionic acid, and the corresponding alkali metal salts.

The ethene oligomerization process may or may not be carried out in the presence of a liquid diluent. Suitable liquid diluents for use in conjunction with the complexed nickel catalysts comprise protic or aprotic polar organic diluents, such as mono- and polyhydric alcohols, in particular aliphatic diols, such as glycol, 1,3-propanediol and 1,4-butanediol; 1,2-alkylene carbonates, such as 1,2-ethylene carbonate, 1,2-propylene carbonate and 2,3-butylene carbonate; and ethers, in particular cyclic ethers such as tetrahydrofuran.

The ethene oligomerization process may be carried out in wide temperature and pressure ranges. Preferred temperatures are in the range of from 0 to 200° C., in particular from 30 to 140° C. Preferred pressures are in the range of from 0.1 to 35 MPa, in particular from 2.5 to 15 MPa.

The oligomerization products may be isolated from the oligomerization reaction mixture by one or more of phase separation, extraction with protic or aprotic polar diluent, extraction with water, and distillation.

The product of the present isomerization process may be worked-up and purified by any suitable method. When a vinylidene olefin is isomerised in the presence of a linear α-olefin, as described hereinbefore, the double bond isomer of the vinylidene olefin may be separated form the linear α-olefin by distillation. The process for treating a linear α-olefin mixture may constitute a purification process for the linear α-olefin as it may yield the linear α-olefin in a more pure form.

Unless specified otherwise, the organic compounds mentioned herein, for example the organic diluents and the ligands, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

The invention will now be illustrated by the following examples.

EXAMPLE 1

A CBV 500 zeolite (trademark) in the form of 1.6 mm (1/16 inch) diameter cylinders, obtained from Zeolyst International, was tested for its ability to catalyse the isomerization of 2-ethyl-1-butene, as follows.

A sample of 1-hexene was prepared by oligomerizing ethene using a nickel catalyst, and working-up by procedures involving extraction with aqueous extraction liquids. Distillation gave the 1-hexene sample as the $C_6$-cut, which contained as impurities 0.55% w of 2-ethyl-1-butene and about 20 ppmw of water.

A sample of the zeolite cylinders was heated at 500° C. in air for a period of 15 hours. A 0.15-g sample was placed in a bottle with 100 ml of the 1-hexene sample. The bottle was shaken during 50 minutes at 20° C. and 0.1 MPa pressure, after which the content of 2-ethyl-1-butene in the 1-hexene was measured. The result is given in Table I.

EXAMPLES 2–4 (FOR COMPARISON)

Example 1 was essentially repeated, except that, instead of the CBV 500 zeolite, samples of the following zeolites were used:
LZ-Y52 zeolite (trademark), a commercially available Y type zeolite in the sodium form which has a pore size of 0.74 nm and a Si/Al atomic ratio of 2.37 (Example 2),
zeolite-13X (Example 3), and
zeolite-4A (Example 4). All zeolite samples were obtained and tested in the form of 1.6 mm (1/16 inch) diameter cylinders.

The results are given in Table I.

EXAMPLES 5–7 (EXAMPLES 7 FOR COMPARISON)

Examples 1 and 2 were essentially repeated, except at prior to placing the CBV 500 zeolite sample or the LZ-Y52 zeolite sample in the bottle with 100 ml 1-hexene, the 1-hexene was pretreated with zeolite-13X (Examples 5 and 7) or zeolite-4A (Example 6), as pretreatment materials, by employing a procedure as outlined in Example 3 or Example 4, and separating the 1-hexane sample from the pretreatment materials. The result is given in Table I.

TABLE I

| Example | Pretreatment(s) | Isomerisation | 2-ethyl-1-butene (% w) |
|---|---|---|---|
| 1 | Distillation*) | CBV 500 zeolite | 0.49 |
| 2**) | Distillation | LZ-Y52 zeolite | 0.55 |
| 3**) | Distillation | zeolite-13X | 0.55 |
| 4**) | Distillation | zeolite-4A | 0.55 |
| 5 | Distillation, contacting with zeolite-13X | CBV 500 zeolite | 0.24 |
| 6 | Distillation, contacting with zeolite-4A | CBV 500 zeolite | 0.36 |
| 7**) | Distillation, contacting with zeolite-13X | LZ-Y52 zeolite | 0.53 |

*)of 1-hexene sample preparation; **)for comparison, not according to the invention

EXAMPLE 8

A sample of zeolite-13X in the form of 1.6 mm (1/16 inch) diameter cylinders was heated in air at 200° C. A first stainless steel cylindrical vessel (about 2.5 cm diameter, about 25 cm height) was filled with this zeolite to form a bed of particles. A sample of CBV 500 zeolite in the form of 1.6 mm (1/16 inch) diameter cylinders was heated in air at 200° C. A second stainless steel cylindrical vessel (about 2.5 cm diameter, about 5 cm height) was filled with the latter zeolite to form a bed of particles.

A flow of a 1-hexene sample similar as employed in Examples 1–7 but containing 0.85% w 2-ethyl-1-butene and having a water content of about 20 ppmw, was maintained through the first vessel, and from the first vessel through the second vessel. In both vessels the flow was up-wards at a rate of 250 g/hour. In the first vessel the temperature was 2° C. and the pressure was 0.5 MPa. In the second vessel the temperature was 40° C. and the pressure was 0.5 MPa. After 36 kg of the 1-hexene sample had passed the vessels the content of 2-ethyl-1-butene in the 1-hexene flow leaving the second vessel was 0.05% w.

EXAMPLE 9

Example 8 was essentially repeated, except that instead of CBV 500 zeolite, a sample of CBV 400 zeolite in the form of 1.6 mm (1/16 inch) diameter cylinders was used. After 36 kg of the 1-hexene sample had passed the vessels the content of 2-ethyl-1-butene in the 1-hexene flow leaving the second vessel was 0.11% w.

EXAMPLE 10

Example 9 was essentially repeated, except that another 1-hexene sample was employed which is similar as the 1-hexene sample employed in Examples 1–7 but containing 0.82% w 2-ethyl-1-butene and having a water content of about 20 ppmw, and that the flow rate was 240 g/hour. After 24 kg of the 1-hexene sample had passed the vessels the content of 2-ethyl-1-butene in the 1-hexene flow leaving the second vessel was 0.50% w.

EXAMPLE 11 (FOR COMPARISON)

Example 10 was essentially repeated, except that instead of CBV 400 zeolite, a sample of CBV 8062 zeolite in the form of 1.6 mm (1/16 inch) diameter cylinders was used.

CBV 8062 zeolite (trademark), obtained from Zeolyst International, is a ZSM-5 type zeolite, in the hydrogen form and it has a Si/Al atomic ratio of 80. After 24 kg of the 1-hexene sample had passed the vessels the content of 2-ethyl-1-butene in the 1-hexene flow leaving the second vessel was 0.62% w.

In the examples it is shown that an improved catalyst performance is accomplished by selecting an isomerization catalyst which comprises a molecular sieve in an acidic form having a pore size of at least 0.6 nm (cf. example 1 vs. example 2, example 5 vs. example 7, examples 8–10 vs. example 11).

In the examples it is also shown that the isomerization catalysts have an improved performance when using as a pretreating material a zeolite which has a large pore size, like zeolite-4A and zeolite-13X (cf. examples 5 and 6 vs. example 1 and example 7 vs. example 2). More specifically, it is shown that the combined use of the pretreating zeolite and the isomerization catalyst leads to a synergistic effect, viz. the combined use has lead to a decrease in vinylidene olefin content which is more than the sum of what was achieved by using only the pretreating zeolites (examples 3 and 4) and what was achieved by using only the isomerization catalysts (examples 1 and 2). This synergistic effect is unobvious and surprising as no such combination has been suggested in the prior art, whilst the pretreating zeolites are known to have isomerization catalyst properties (cf. U.S. Pat. No. 4,697,040 and U.S. Pat. No. 3,686,250) and isomerization catalysts may be used as a pretreating material (cf. U.S. Pat. No. 3,686,250).

We claim:

1. A process for the double bond isomerization of a vinylidene olefin, comprising 1) pretreating a feed comprising the vinylidene olefin with pretreating material which comprises a zeolite having a pore size of at least 0.35 nm and then 2) contacting the feed with an isomerization catalyst which comprises a molecular sieve in an acidic form, which molecular sieve comprises pores which have a pore size of at least 0.7 nm.

2. The process of claim 1 wherein the vinylidene olefin is of the general formula $CH^2=C(R^1)R^2$, wherein $R^1$ represents an ethyl group and $R^2$ represents a linear 1-alkyl group, and the feed comprises a linear α-olefin which is isomeric to the vinylidene olefin.

3. The process of claim 2 wherein $R^2$ represents a linear 1-alkyl group having an even number of carbon atoms.

4. The process of claim 1 wherein the pore size of the molecular sieve of the isomerization catalyst is at least 0.7 nm and at most 0.9 nm.

5. The process of claim 1 wherein the molecular sieve of the isomerization catalyst is a zeolite having a silicon/aluminum atomic ratio of at least 1.3 and at most 20.

6. The process of claim 5 wherein the molecular sieve of the isomerization catalyst is a zeolite having a silicon/aluminum atomic ratio of at least 1.5 and at most 8.

7. The process of claim 1 wherein the molecular sieve of the isomerization catalyst is in the hydrogen form.

8. The process of claim 1 wherein the molecular sieve has a faujasite structure.

9. The process of claim 1 wherein the vinylidene olefin is of the general formula $CH_2=C(R^1)R^2$ wherein $R^1$ represents an ethyl group and $R^2$ represents a linear 1-alkyl group, and wherein the isomerization catalyst comprises a molecular sieve other than a mordenite zeolite in the ammonium form.

10. The process of claim 1 wherein the vinylidene olefin is of the general formula $CH_2=C(R^1)R^2$ wherein $R^1$ represents an ethyl group and $R^2$ represents a linear 1-alkyl group having an even number of carbon atoms, and wherein the isomerization catalyst comprises a molecular sieve other than a mordenite zeolite in the ammonium form.

11. The process of claim 1 wherein the components of the feed are pretreated together as a mixture.

12. The process of claim 1 wherein the zeolite of the pretreating material is in the sodium form or calcium and has a pore size of at least 0.5 nm and at most 1.5 nm.

13. The process of claim 1 wherein the molecular sieve of the isomerization catalyst is in the hydrogen form and has a pore size of at least 0.65 nm and at most 1 nm.

14. The process of claim 1 wherein the molecular sieve of the isomerization catalyst is in the hydrogen form and has a pore size of at least 0.65 nm and at most 1 nm, and wherein the zeolite of the pretreating material is in the sodium form or calcium form and has a pore size of at least 0.5 nm and at most 1.5 nm.

15. A process for treating an olefin mixture which comprises a linear α-olefin and a vinylidene olefin which is isomeric to the linear α-olefin and which is of the general formula $CH_2=C(R^1)R^2$, wherein $R^1$ represents an ethyl group and $R^2$ represents a linear 1-alkyl group, which process comprises 1) pretreating the olefin mixture by contacting it with pretreating material which comprises a zeolite having a pore size of at least 0.35 nm and 2) isomerizing the vinylidene olefin to form a double bond isomer of the vinylidene olefin by contacting a feed comprising the olefin mixture with an isomerization catalyst which comprises a molecular sieve in an acidic form, which molecular sieve comprises pores which have a pore size of at least 0.7 nm, and separating the linear α-olefin from the double bond isomer of the vinylidene olefin.

16. The process of claim 15 wherein the molecular sieve of the isomerization catalyst is in the hydrogen form and has a pore size of at least 0.7 nm and at most 0.9 nm, and wherein the zeolite of the pretreating material is in the sodium form or calcium form and has a pore size of at least 0.5 nm and at most 1.5 nm.

17. The process of claim 16 wherein the linear α-olefin is separated from the double bond isomer of the vinylidene olefin by distillation.

* * * * *